(12) United States Patent
Hashimoto et al.

(10) Patent No.: US 12,171,513 B2
(45) Date of Patent: Dec. 24, 2024

(54) SURGICAL SYSTEM AND PATIENT-SIDE APPARATUS

(71) Applicant: KAWASAKI JUKOGYO KABUSHIKI KAISHA, Kobe (JP)

(72) Inventors: Yasuhiko Hashimoto, Kobe (JP); Toshiaki Yoshida, Kobe (JP); Wataru Doi, Kobe (JP)

(73) Assignee: KAWASAKI JUKOGYO KABUSHIKI KAISHA, Kobe (JP)

( * ) Notice: Subject to any disclaimer, the term of this patent is extended or adjusted under 35 U.S.C. 154(b) by 849 days.

(21) Appl. No.: 16/591,638

(22) Filed: Oct. 3, 2019

(65) Prior Publication Data

US 2020/0107895 A1 Apr. 9, 2020

(30) Foreign Application Priority Data

Oct. 5, 2018 (JP) .................................. 2018-189825
Sep. 20, 2019 (JP) .................................. 2019-171956

(51) Int. Cl.
*A61B 34/35* (2016.01)
*A61B 34/00* (2016.01)
(Continued)

(52) U.S. Cl.
CPC .............. *A61B 34/35* (2016.02); *A61B 34/20* (2016.02); *A61B 34/25* (2016.02); *A61B 34/76* (2016.02);
(Continued)

(58) Field of Classification Search
CPC ......... A61B 34/35; A61B 34/20; A61B 34/25; A61B 34/76; A61B 90/50;
(Continued)

(56) References Cited

U.S. PATENT DOCUMENTS

2005/0166413 A1  8/2005 Crampton
2006/0167440 A1  7/2006 Cooper et al.
(Continued)

FOREIGN PATENT DOCUMENTS

JP   2008-018240 A   1/2008
JP   2013-034830 A   2/2013
(Continued)

*Primary Examiner* — Richard G Louis
(74) *Attorney, Agent, or Firm* — METROLEX IP LAW GROUP, PLLC; Robert L. Scott, Esq.

(57) ABSTRACT

A patient-side apparatus of a surgical system according to an embodiment may include: manipulator arms with multi-degree of freedom, each of which includes a distal end portion provided with a tool holding part configured to hold an elongated surgical tool; an arm base to which base end portions of the manipulator arms are attached; a base; and a positioner that includes links and joints to connect the base and the arm base such that the positioner movably holds the arm base. The links include a first link that is connected to a central portion of the arm base in a longitudinal direction of the arm base with a first roll joint arranged between the first link and the arm base. The positioner holds the arm base such that a first rotation axis of the first roll joint is inclined with respect to both a vertical direction and a horizontal plane.

17 Claims, 6 Drawing Sheets (51) Int. Cl.
*A61B 34/20* (2016.01)
*A61B 90/50* (2016.01)
*A61B 17/00* (2006.01)

(52) U.S. Cl.
CPC .... *A61B 90/50* (2016.02); *A61B 2017/00207* (2013.01)

(58) Field of Classification Search
CPC .... A61B 2017/00207; A61B 2090/508; A61B 34/37; A61B 34/30; A61B 90/361; A61B 2034/2059
See application file for complete search history.

(56) References Cited

U.S. PATENT DOCUMENTS

| | | | |
|---|---|---|---|
| 2007/0142825 A1* | 6/2007 | Prisco | A61B 34/70 606/1 |
| 2008/0013692 A1 | 1/2008 | Maschke | |
| 2010/0224022 A1 | 9/2010 | Choi et al. | |
| 2013/0144307 A1* | 6/2013 | Jeong | A61B 90/10 606/130 |
| 2014/0052153 A1* | 2/2014 | Griffiths | A61B 34/70 606/130 |
| 2014/0135795 A1 | 5/2014 | Yanagihara | |
| 2014/0180308 A1 | 6/2014 | von Grünberg | |
| 2014/0249546 A1 | 9/2014 | Shvartsberg et al. | |
| 2017/0079730 A1 | 3/2017 | Azizian et al. | |
| 2017/0165837 A1 | 6/2017 | Asano et al. | |
| 2017/0172674 A1 | 6/2017 | Hanuschik et al. | |
| 2017/0172676 A1* | 6/2017 | Itkowitz | A61B 34/35 |
| 2019/0046279 A1* | 2/2019 | Hille | A61B 90/50 |
| 2019/0069963 A1 | 3/2019 | Azizian et al. | |

FOREIGN PATENT DOCUMENTS

| | | |
|---|---|---|
| JP | 2016-505316 A | 2/2016 |
| JP | 2017-104456 A | 6/2017 |
| JP | 2017-513550 A | 6/2017 |
| JP | 2017-515524 A | 6/2017 |
| WO | 2013/078529 A1 | 6/2013 |

* cited by examiner

SURGICAL SYSTEM AND PATIENT-SIDE APPARATUS

CROSS REFERENCE TO RELATED APPLICATIONS

This application claims priority to Japanese Patent Application No. 2018-189825 filed on Oct. 5, 2018 and Japanese Patent Application No. 2019-171956 filed on Sep. 20, 2019, the entire contents of which are incorporated herein by reference.

BACKGROUND

The disclosure may relate to a surgical system and a patient-side apparatus for a surgical system.

There has been known a master-slave type surgical system that includes multiple manipulator arms and performs surgery by moving the manipulator arms operated by a surgeon (for example, see Documents 1 and 2). In such a system, the manipulator arms are arranged close to each other so that the manipulator arms can cooperate to perform a delicate procedure on a single surgery site.

As disclosed in Documents 1 and 2, base end portions of the manipulator arms of a general surgical system are thus attached to a single arm base (or, also referred to as a platform). The arm base is arranged by using a positioner so as to be hung above (directly above) a surgery site of a patient.

Document 1: Published Japanese Translation of PCT International Application No. 2017-515524
Document 2: Published Japanese Translation of PCT International Application No. 2017-513550

SUMMARY

In such a surgery system, the arm base to which the base end portions of the manipulator arms are attached is set at a position higher than the height of an operator such as the surgeon or the like directly above the surgery site. Accordingly, when the operator sets, upon preparing the surgery, the arm base to a certain position over the patient lying on an operating table (a surgical bed), the operator needs to move downwardly the arm base from the position higher than the height of the operator. This may make the operator who performs preparation of the surgery feel oppressed.

An object of one or more embodiments may be to provide a surgical system and a patient-side apparatus, which make an operator who performs preparation of the surgery less oppressed at a surgery site.

A patient-side apparatus of a surgical system according to an aspect of one or more embodiments may include: manipulator arms with multi-degree of freedom, each of which includes a distal end portion provided with a tool holding part configured to hold an elongated surgical tool; an arm base to which base end portions of the manipulator arms are attached; a base; and a positioner that includes links and joints to connect the base and the arm base such that the positioner movably holds the arm base. The links include a first link that is connected to a central portion of the arm base in a longitudinal direction of the arm base with a first roll joint arranged between the first link and the arm base. The positioner holds the arm base such that a first rotation axis of the first roll joint is inclined with respect to both a vertical direction and a horizontal plane.

According to the first aspect, the first rotation axis of the first joint of the positioner can be directed to a surgery site or the vicinity of the surgery site in a state where the arm base is positioned obliquely above the surgery site. Consequently, it may be possible to set the positions of the arm base and the positioner in the horizontal direction in positions offset from the surgery site in the horizontal direction. This can make an operator who performs preparations of the surgery less oppressed by the positioner and the arm base.

A surgical system according to a second aspect of one or more embodiments may include: a patient-side apparatus including manipulator arms with multi-degree of freedom, each of which includes a distal end portion provided with a tool holding part configured to hold an elongated surgical tool; and an operation apparatus to remotely control the manipulator arms. The patient-side apparatus according to the second aspect may include: an arm base to which base end portions of the manipulator arms are connected; a base; and a positioner that includes links and joints to connect the base and the arm base such that the positioner movably holds the arm base. The links include a first link that is connected to a central portion of the arm base in a longitudinal direction of the arm base with a first roll joint arranged between the first link and the arm base. The positioner holds the arm base such that a first rotation axis of the first roll joint is inclined with respect to both a vertical direction and a horizontal plane.

According to the second aspect, the first rotation axis of the first joint of the positioner can be directed to a surgery site or the vicinity of the surgery site in a state where the arm base is positioned obliquely above the surgery site. Consequently, it may be possible to set the positions of the arm base and the positioner in the horizontal direction in positions offset from the surgery site in the horizontal direction. This can make an operator who performs preparations of the surgery less oppressed by the positioner and the arm base.

According to the aspects described above, it may be possible to make an operator who performs preparations of the surgery less oppressed by the positioner and/or the arm base.

An object, characteristics, and advantages of the invention may be apparent from the detailed descriptions of the one or more embodiments below with reference to the accompanying drawings.

DETAILED DESCRIPTION

Descriptions are provided hereinbelow for one or more embodiments based on the drawings. The invention is not limited to the one or more embodiments. In the respective drawings referenced herein, the same constituents are designated by the same reference numerals and duplicate explanation concerning the same constituents is omitted. All of the drawings are provided to illustrate the respective examples only.

Figure 1:
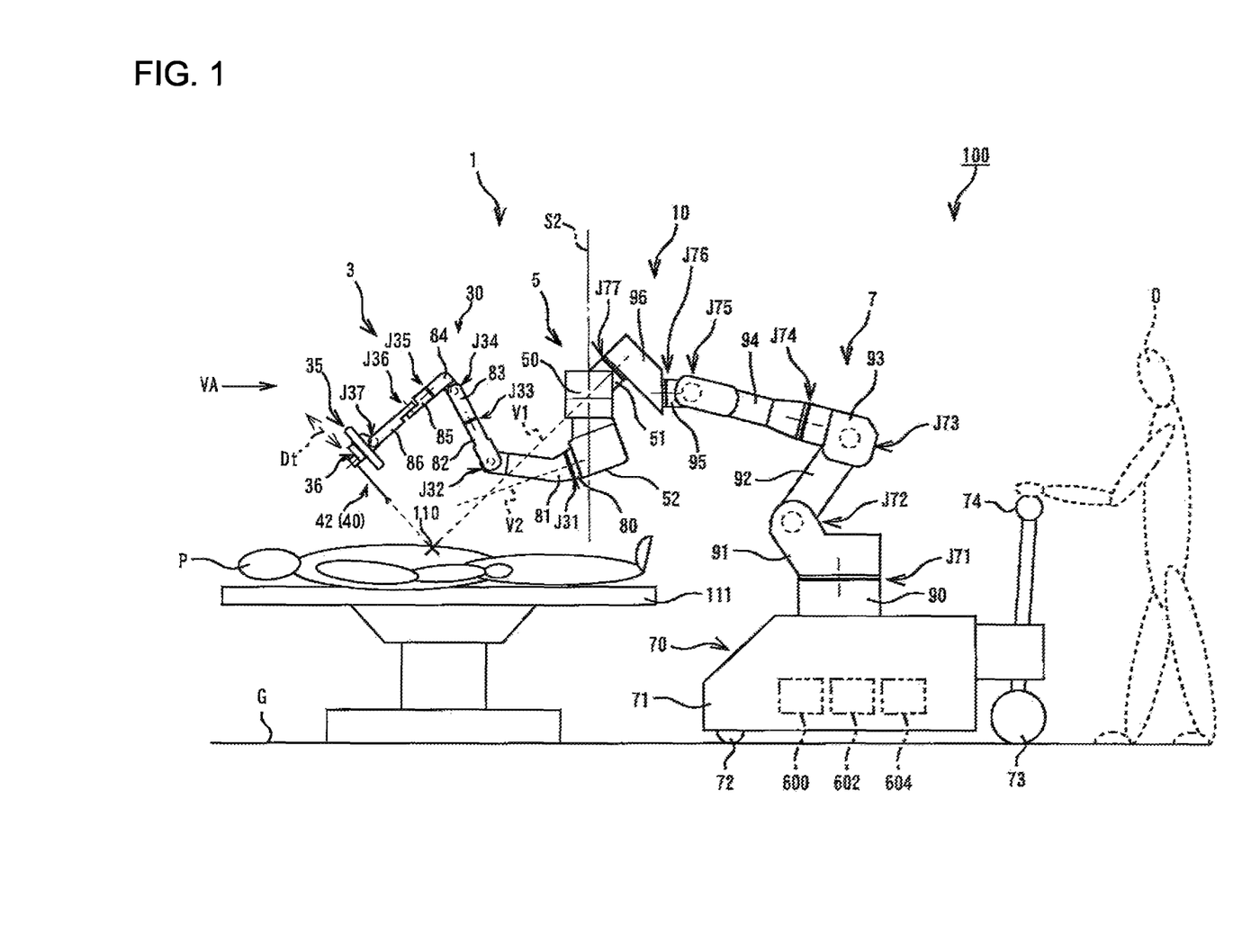
FIG. 1 is a diagram illustrating a schematic view of an overall configuration of a surgical system according to one or more embodiments.

FIG. 1 is a diagram illustrating a schematic view of an overall configuration of a surgical system according to one or more embodiments. A surgical system 100 is a system for a surgeon such as a doctor to perform endoscopic surgery on a patient P with a patient-side system 1 (a patient-side apparatus), like robotic-assistant surgery and robotic tele-surgery. FIG. 1 illustrates a state in which a positioner 7, an arm base 5, and manipulator arms 3 are set in a predetermined preparation position that is determined before procedure (details are described later). In FIG. 1, the ratio of the size of the illustrated manipulator arms 3 to the positioner 7 is different from the actual ratio. The actual ratio of the size of the manipulator arms 3 to the positioner 7 is smaller than the configuration illustrated in FIG. 1.

The surgical system 100 includes the patient-side system 1 and an operation apparatus 2 serving as an instruction apparatus (see FIG. 4 described later) for controlling the manipulator arms 3 of the patient-side system 1. The operation apparatus 2 is disposed apart from the patient-side system 1, and the manipulator arms 3 of the patient-side system 1 are remotely controlled by the operation apparatus 2 during procedure. The surgeon inputs an action to be executed by each of the manipulator arms 3 of the patient-side system 1 to the operation apparatus 2, and the operation apparatus 2 transmits the action instruction to the patient-side system 1. The patient-side system 1 receives the action instruction transmitted from the operation apparatus 2. Based on the action instruction, the patient-side system 1 operates a tool such as an elongated surgical tool 40 held by the manipulator arm 3 of the patient-side system 1.

The operation apparatus 2 is an apparatus constructing an interface between the surgical system 100 and the surgeon so as to control the manipulator arms 3 of the patient-side system 1. The operation apparatus 2 is disposed nearby or away from an operating table 111 (a surgical bed) in a surgery room or disposed outside of the surgery room. Although it is not illustrated, the operation apparatus 2 includes operation input units such as an operation manipulator arm and an operation pedal for the surgeon to input the action instruction, and a monitor that displays an image captured by an endoscope assembly (not illustrated) as the surgical tool 40 attached to the patient-side system 1. The surgeon operates the operation input units to input the action instruction to the operation apparatus 2 while visually checking an affected area (a surgery site 110) through the monitor. The action instruction inputted to the operation apparatus 2 is transmitted to the later-described controller 600 of the patient-side system 1 through wired or wireless communications.

The patient-side system 1 constructs an interface between the surgical system 100 and the patient P. In the surgery room, the patient-side system 1 is disposed nearby the operating table 111 on which the patient P is laid. Inside of the surgery room is sterilized to be a sterile field.

The patient-side system 1 includes the positioner 7, the arm base (platform) 5 attached to the distal end portion of the positioner 7, and the patient-side manipulator arms (hereinafter, simply referred to as "arms 3") detachably attached to the arm base 5. The positioner 7 is a device extending from a base to connect the base with the arm base 5. In this embodiment, the positioner 7 is formed as an articulated robot having seven degrees of freedom. The positioner 7 can move the position of the arm base 5 three-dimensionally with respect to a movable wagon 70, which is the base. The positioner 7 and the arm base 5 are covered with sterile drapes (not-illustrated) and shielded from the sterile field in the surgery room. In a perspective of increasing the degrees of freedom of arrangement of the arm base 5, the positioner 7 is preferably configured as an articulated robot having six or more degrees of freedom.

The distal end portion of each of the arms 3 is configured as a tool holding part (a holder 36) that can hold the surgical tool 40. The distal end portion of one of the arms 3 holds the endoscope assembly (not illustrated). The distal end portion of the rest of the arms 3 detachably holds an instrument 42. Hereinafter, the arm 3 to which the endoscope assembly is attached may be referred to as a "camera arm," and the arm 3 to which the instrument 42 is attached may be referred to as an "instrument arm." The patient-side system 1 in this embodiment includes four arms 3 including one camera arm and three instrument arms.

In the above-described patient-side system 1, the arm base 5 serves as a "hub" that is a base of the arms 3. In this embodiment, the positioner 7 and the arm base 5 form a manipulator arm support body 10 that movably supports the arms 3.

In the above-described patient-side system 1, the elements from the positioner 7 to the endoscope assembly or the instrument 42 are connected in series. In this disclosure, in each of the series of elements, an end portion close to the positioner 7 (more specifically, a base 90 that is a connection portion between the positioner 7 and the wagon 70) is referred to as the "base end portion," and an end portion on the opposite side is referred to as the "distal end portion."

The wagon 70, the positioner 7, the arm base 5, and the manipulator arms 3 are described in detail below.

As illustrated in FIG. 1, the wagon 70 includes a wagon body 71, front wheels 72 and rear wheels 73, and a handle 74. The front wheels 72 and the rear wheels 73 are rotatably attached to the wagon body 71, and the wagon body 71 is thus configured to be movable. The rear wheels 73 are configured to be turnable about a rotational axis of the handle 74, and this makes it possible to change a traveling direction of the wagon body 71 with the surgeon or a surgical assistant O grasping and turning the handle 74 about the rotational axis.

Operation of the patient-side system 1 is controlled by the controller 600. The controller 600 is formed of a computer such as a microcontroller, for example. The controller 600 and a storage 602 in which a control program and various kinds of data used for the operation control are stored are housed inside the wagon body 71. The wagon body 71 is also provided with an operation unit 604, which is mainly for setting and inputting the position and orientation of the positioner 7, the arm base 5, and the arms 3 before procedure (the later-described preparation orientation). The operation unit 604 is formed of a touch panel and the like, for example. The positioner 7 can move the arm base 5 based on the input through the operation unit 604.

The positioner 7 includes the base 90 attached to the wagon body 71 and positioner link portions subsequently connected with each other from the base 90 toward the distal end portion. With one positioner link portion rotatably connected to another positioner link unit subsequently, the positioner 7 forms multiple joint portions. The positioner link portions include a first link 91 to a sixth link 96. The joint portions include a first joint J71 to a seventh joint J77. Each of the joint portions in this embodiment is formed of a joint having a rotation axis; however, at least one or more of the joint portions may be formed of a direct-acting joint.

More specifically, the base end portion of the first link 91 is connected to the distal end portion of the base 90 with the first joint J71 as a roll joint arranged therebetween. In this disclosure, a roll joint may be defined as a joint that connects two objects such that a distal side object can rotate (roll) with respect to a proximal side object about a rotation axis of the joint (also referred to as a roll axis). The base end portion of the second link 92 is connected to the distal end portion of the first link 91 with the second joint J72 as a pivotal (pitch) joint arranged therebetween. The base end portion of the third link 93 is connected to the distal end portion of the second link 92 with the third joint J73 as a pivotal joint arranged therebetween. In this disclosure, a pivotal joint may be defined as a joint that connects two objects such that an angle between the distal side object with respect to the proximal object can be changed about a rotation axis of the joint (also referred to a pitch axis). The base end portion of the fourth link 94 is connected to the distal end portion of the third link 93 with the fourth joint J74 as a roll joint arranged therebetween. The base end portion of the fifth link 95 is connected to the distal end portion of the fourth link 94 with the fifth joint J75 as a pivotal joint arranged therebetween. The base end portion of the sixth link 96 is connected to the distal end portion of the fifth link 95 with the sixth joint J76 as a roll joint arranged therebetween. A positioner attachment portion 51 of the arm base 5 is connected to the distal end portion of the sixth link 96 with the seventh joint J77 as a roll joint arranged therebetween. Thus, the positioner 7 is formed as a multi-axis joint (seven-axis joint) arm having the multi-degree of freedom (seven degrees of freedom).

As described above, in the sixth link 96 as a positioner link portion attached to the positioner attachment portion 51 of the arm base 5, both the sixth joint J76 as a joint portion on the base end side and the seventh joint J77 as a joint portion on the distal end side are formed as the roll joints. In addition, the rotation axis of the sixth joint J76 is relatively inclined with respect to the rotation axis of the seventh joint J77. More specifically, the rotation axis of the sixth joint J76 is inclined with respect to the longitudinal direction of the sixth link 96, while the rotation axis of the seventh joint J77 is orthogonal to the longitudinal direction of the sixth link 96. An extension of the rotation axis of the sixth joint J76 and an extension of the rotation axis of the seventh joint J77 cross each other. That is, the surface of revolution of the sixth joint J76 is inclined with respect to the surface of revolution of the seventh joint J77.

The arm base 5 includes an arm base body 50, the positioner attachment portion 51 that is attached to the top (on the base end side) of the arm base body 50 with the distal end portion of the positioner 7 attached to the positioner attachment portion 51, and at least one arm attachment portion 52 that is attached to the bottom (on the distal end side) of the arm base body 50 with the base end portions of the arms 3 attached to the arm attachment portion 52. The arm base 5 is configured to be relatively rotatable with respect to the distal end portion of the positioner 7 (the sixth link 96) about the rotation axis V1 of the seventh joint J77, serving as a first rotation axis V1. In this embodiment, multiple (four) arm attachment portions 52 are provided in accordance with the multiple (four) arms 3. Bases 80 of the arms 3 are respectively secured to the arm attachment portions 52. Thus, the base end portion of each arm 3 (the later-described first link 81) is configured to be relatively rotatable about a rotation axis V2 of the later-described first joint J31, serving as a second rotation axis V2. A more specific configuration of the arm base 5 is described later.

Figure 2:
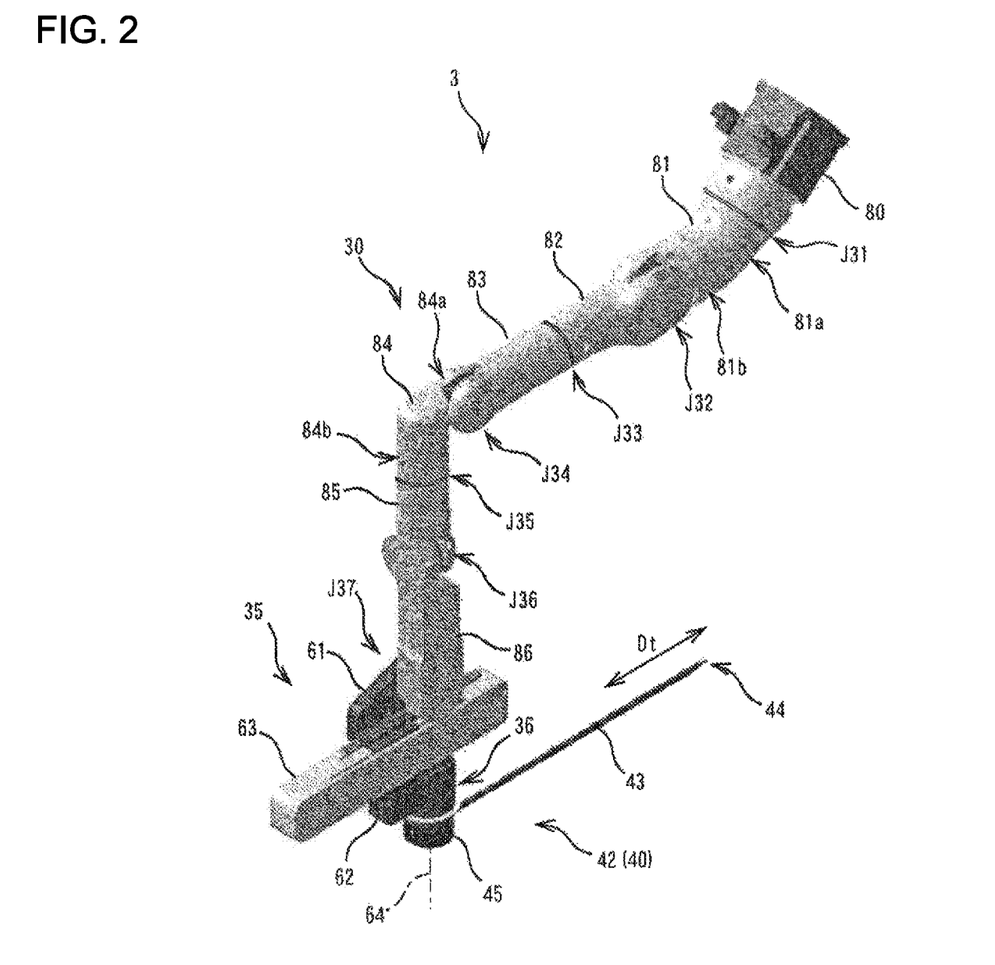
FIG. 2 is a diagram illustrating a schematic view of an overall configuration of a manipulator arm of the surgical system illustrated in FIG. 1.

FIG. 2 is a schematic view of an overall configuration of the manipulator arm of the surgical system illustrated in FIG. 1. FIG. 2 illustrates a schematic configuration of a single arm 3 to which the instrument 42 is attached, the single arm 3 being out of the multiple arms 3 provided to the patient-side system 1. In this embodiment, the arms 3 provided to the patient-side system 1 have the same or similar configurations; however, at least one of the arms 3 may have a different configuration from the other arms (for example, may have different degrees of freedom, or the like). As illustrated in FIG. 2, the arm 3 includes an arm body 30 and a translation unit 35 connected to the distal end portion of the arm body 30. The arm 3 is formed such that the distal end portion thereof is three-dimensionally movable with respect to the corresponding base end portion. The distal end portion of the arm 3 is provided with the holder (the tool holding unit) 36 that can hold the elongated surgical tool 40 (the instrument 42 or the endoscope assembly). In this embodiment, the holder 36 is provided to the translation unit 35.

The instrument 42 includes a drive unit 45 provided to the base end portion, an end effector (procedure tool) 44 provided to the distal end portion, and an elongated shaft 43 connecting the drive unit 45 and the end effector 44. The drive unit 45, the shaft 43, and the end effector 44 are arranged along an axis direction Dt or a longitudinal direction of the instrument 42. The end effector 44 of the instrument 42 is selected from a group including a tool having a movable joint (for example, pair of forceps, pair of scissors, grasper, needle holder, micro dissector, staple applier, tacker, suction and irrigation tool, snare wire, clip applier, and so on) and a tool having no joints (for example, cutting blade, ablation probe, irrigation device, catheter, suction orifice, and so on).

When the arm 3 is the instrument arm, the holder 36 detachably holds the instrument 42. A shaft 43 of the instrument 42 held by the holder 36 extends along the axis direction Dt. On the other hand, when the arm 3 is the camera arm, the holder 36 detachably holds the endoscope assembly. In this case, the holder 36 provided to the camera arm may have a different shape or configuration from that of the holder 36 provided to the instrument arm. In addition, since it is rare to make replacement of the endoscope assembly during surgery, the endoscope assembly may be secured to the camera arm.

The arm 3 is configured to be attachable to and detachable from the arm base 5. The arm 3 has resistances for irrigation processing and sterile processing, including water resistance, heat resistance, and chemical resistance. There are various ways for the sterile processing of the arm 3. For example, autoclave sterilization, EOG sterilization, chemical sterilization with an antiseptic, and so on may be selectively used.

The arm body 30 includes a base 80 detachably attached to the arm base 5 and arm link portions sequentially connected with each other from the base 80 toward the distal end portion. With one arm link portion rotatably connected to another arm link portion sequentially, the arm 3 forms multiple joint portions. The arm link portions include the first link 81 to a seventh link 87. The joint portions include the first joint J31 to a seventh joint J37. Each of the joint portions in this embodiment is formed of a rotation joint having a rotation axis; however, at least a part of the joint portions may be formed of a direct-acting joint.

More specifically, the base end portion of the first link 81 is connected to the distal end portion of the base 80 with the first joint J31 as a roll joint arranged therebetween. The base end portion of the second link 82 is connected to the distal end portion of the first link 81 with the second joint J32 as a pivotal joint arranged therebetween. The base end portion of the third link 83 is connected to the distal end portion of the second link 82 with the third joint J33 as a roll joint arranged therebetween. The base end portion of the fourth link 84 is connected to the distal end portion of the third link 83 with the fourth joint J34 as a pivotal joint arranged therebetween. The base end portion of the fifth link 85 is connected to the distal end portion of the fourth link 84 with the fifth joint J35 as a roll joint arranged therebetween. The base end portion of the sixth link 86 is connected to the distal end portion of the fifth link 85 with the sixth joint J36 as a pivotal joint arranged therebetween. The base end portion of the translation unit 35 is connected to the distal end portion of the sixth link 86 with the seventh joint J37 as a pivotal joint arranged therebetween. Thus, the arm 3 is formed as a multi-axis joint (seven-axis joint) arm having the multi-degree of freedom (seven degrees of freedom). Consequently, the arm 3 can change the overall orientation thereof without changing the position and orientation of the distal end portion of the arm 3.

In this embodiment, the first link 81 has a bending shape between the joints J31 and J32 next to each other. In other words, the first link 81 is formed such that the rotation axis of the first joint J31 and the rotation axis of the second joint J32 do not cross each other. That is, the first link 81 includes a first portion 81*a* and a second portion 81*b*. The first portion 81*a* extends in a predetermined first direction (a rotation axis direction of the first joint J31) from the first joint J31 on the base end side. The second portion 81*b* extends in a second direction crossing the extending direction of the first portion 81*a* (the second direction also being a direction orthogonal to the second joint J32) from the distal end portion of the first portion 81*a* to be connected to the second joint J32 on the distal end side. An angle formed by the first direction and the second direction at the first link 81 is, for example, 120 degrees or more and 160 degrees or less (for example, 140 degrees). The first portion 81*a* and the second portion 81*b* are smoothly connected with each other. This makes it possible to easily arrange wires (not illustrated) such as electric wirings in the arm link portions although one of the arm link portions has the bending shape.

In addition, the fourth link 84 has a bending shape between the joints J34 and J35 next to each other. In other words, the fourth link 84 is formed such that the rotation axis of the fourth joint J34 and the rotation axis of the fifth joint J35 do not cross each other. That is, the fourth link 84 includes a first portion 84*a* and a second portion 84*b*. The first portion 84*a* extends in a first direction (a direction orthogonal to both the rotation axis of the fourth joint J34 and the rotation axis of the fifth joint J35) from the fourth joint J34 on the base end side. The second portion 84*b* extends in a second direction crossing the extending direction of the first portion 84*a* (a rotation axis direction of the fifth joint J35) from the distal end portion of the first portion 84*a* to be connected to the fifth joint J35 on the distal end side. An angle formed by the first direction and the second direction at the fourth link 84 is, for example, 70 degrees or more and 110 degrees or less (for example, 90 degrees). The first portion 84*a* and the second portion 84*b* are smoothly connected with each other.

Figure 3:
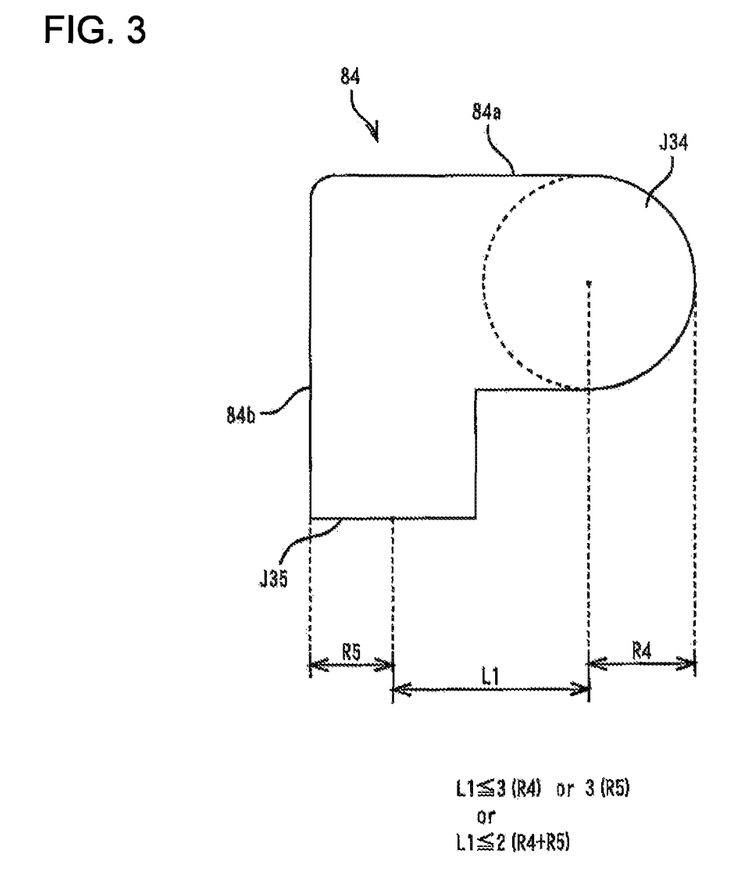
FIG. 3 is a diagram illustrating a side view schematically illustrating an example of a fourth link illustrated in FIG. 2.

Specifically, the fourth link 84 is formed to have the link length shorter than those of the other joint portions. FIG. 3 is a side view schematically illustrating an example of the fourth link 84 illustrated in FIG. 2. As illustrated in FIG. 3, for example, the fourth link 84 is formed such that a length L1 in the first direction between the rotation axis of the fourth joint J34 and the rotation axis of the fifth joint J35 is no more than four times, or more preferably no more than three times, of a radius R4 of the fourth joint J34 or a radius R5 of the fifth joint J35. The radius R4 of the fourth joint J34 is defined as a distance between the rotation axis of the fourth joint J34 and a position of the base end portion of the fourth link 84 in the first direction. The radius R5 of the fifth joint J35 is defined as a distance between the rotation axis of the fifth joint J35 and a position of the distal end portion of the fourth link 84 in the first direction. The fourth link 84 is formed such that the length L1 is no more than two times of the sum of the radius R4 of the fourth joint J34 and the radius R5 of the fifth joint J35. More preferably, the above-described length L1 is shorter than a length obtained by adding the radius R5 of the fifth joint J35, which is the shorter one between the radius R4 of the fourth joint J34 and the radius R5 of the fifth joint J35, to the sum of the radius R4 of the fourth joint J34 and the radius R5 of the fifth joint J35.

The other links 82, 83, 85, and 86 are each formed in a straight line shape between the joint portions next to each other. In other words, the other links 82, 83, 85, and 86 are formed such that the rotation axes of the joint portions next to each other cross each other.

The arm link portions are formed such that one arm link portion has the smaller area of a cross section orthogonal to the longitudinal direction than that of the other arm link portion (or the base 80) connected on the base end side of the one arm link portion. Accordingly, the arm 3 is formed to be gradually narrower from the base end portion toward the distal end portion. In addition, the joints J32, J34, and J36 as the pivotal joints are formed as follows. The distal end portion of each of the arm link portions 81, 83, and 85 on the base end side is positioned on one side in the rotation axis direction relative to a middle portion in the rotation axis direction in the corresponding joint portion. Meanwhile, the base end portion of each of the arm link portions 82, 84, and 86 on the distal end side is positioned on the other side in the rotation axis direction relative to the middle portion in the rotation axis direction in the corresponding joint portion, such that the base end portions of the arm link portions 82, 84, and 86 face the distal end portions of the arm link portions 81, 83, and 85, respectively. That is, these joints J32, J34, and J36 are formed by the halved joint.

Besides, a width of each joint portion in the rotation axis direction is shorter than a diameter (the maximum dimension) of a cross section of a portion closer to the base end portion of corresponding one of the arm link portions 81, 83, and 85 on the base end side, the cross section being orthogonal to the longitudinal direction. The width of the joint portion is a distance between an outer end portion in the rotation axis direction of the distal end portion of corresponding one of the arm link portions 81, 83, and 85 on the base end side and an outer end portion in the rotation axis direction of the base end portion of corresponding one of the arm link portions 82, 84, and 86 on the distal end side.

As described above, each joint portion and the arm link portion on the distal end side of the joint portion is formed narrower than the arm link portion on the base end side. This makes it possible to increase a moving range of the arm 3 (a range in which the arm 3 does not interfere with the other) in a work space that becomes narrower as the arm 3 comes closer to the surgery site 110 of the patient P.

An outer shell of the arm body 30 is formed of a member having heat resistance and chemical resistance, such as mainly stainless. An opening portion of the arm body 30 such as an inspection hole is covered with a resin cover. With the cover formed of a member such as resin, it is possible to achieve weight reduction of a portion that does not contribute the strength of the arm 3. Consequently, it is possible to reduce the accidental impact caused when the cover falls off or when the arm 3 hits another arm 3 or the surgical assistant O, for example. The outer shell itself of the arm body 30 may include a portion formed of a resin member. A connection portion between the links is provided with sealing (not illustrated) to provide water resistance. The sealing has the heat resistance for autoclaved sterilization and the chemical resistance for antiseptic. In the connection portion between the links, an end portion of one link is inserted into an end portion of the other link to be connected with the one link, and the sealing is arranged so as to fill the space between the end portions of the links. Thus, the sealing is hidden from external appearance. In this way, entering of water, chemical liquid, and vapor through the space between the sealing and the link is suppressed.

The translation unit 35 is a mechanism that translationally moves the instrument 42 attached to the holder 36 in the extending direction of the shaft 43 by translationally moving the holder 36 attached to the distal end portion of the translation unit 35 in the axis direction Dt.

The translation unit 35 includes a base end side link 61 that is connected to the distal end portion of the sixth link 86 of the arm body 30 with the seventh joint J37 as a pivotal joint arranged therebetween, a distal end side link 62, a connection link 63 that moves between the base end side link 61 and the distal end side link 62 in an interlocking manner, and an interlocking mechanism (not illustrated). The seventh joint J37 extends in a direction orthogonal to the axis direction Dt. In addition, a rotational axis 64 is provided at the distal end portion of the translation unit 35 or the distal end portion of the distal end side link 62. A drive source of the translation unit 35 is provided to the base end side link 61. The connection link 63 extends along the axis direction Dt.

In the translation unit 35, the interlocking mechanism allows changings of relative positions of the base end side link 61 and the connection link 63 in the axis direction Dt and relative positions of the connection link 63 and the distal end side link 62 in the axis direction Dt, and accordingly it is possible to change a position of the instrument 42 attached to the holder 36 provided to the distal end side link 62 in the axis direction Dt with respect to the base end side link 61. A publicly known link mechanism can be employed as the interlocking mechanism. The interlocking mechanism may have a configuration using a pulley and a timing belt or may be a mechanism including a gear train, for example.

Figure 4:
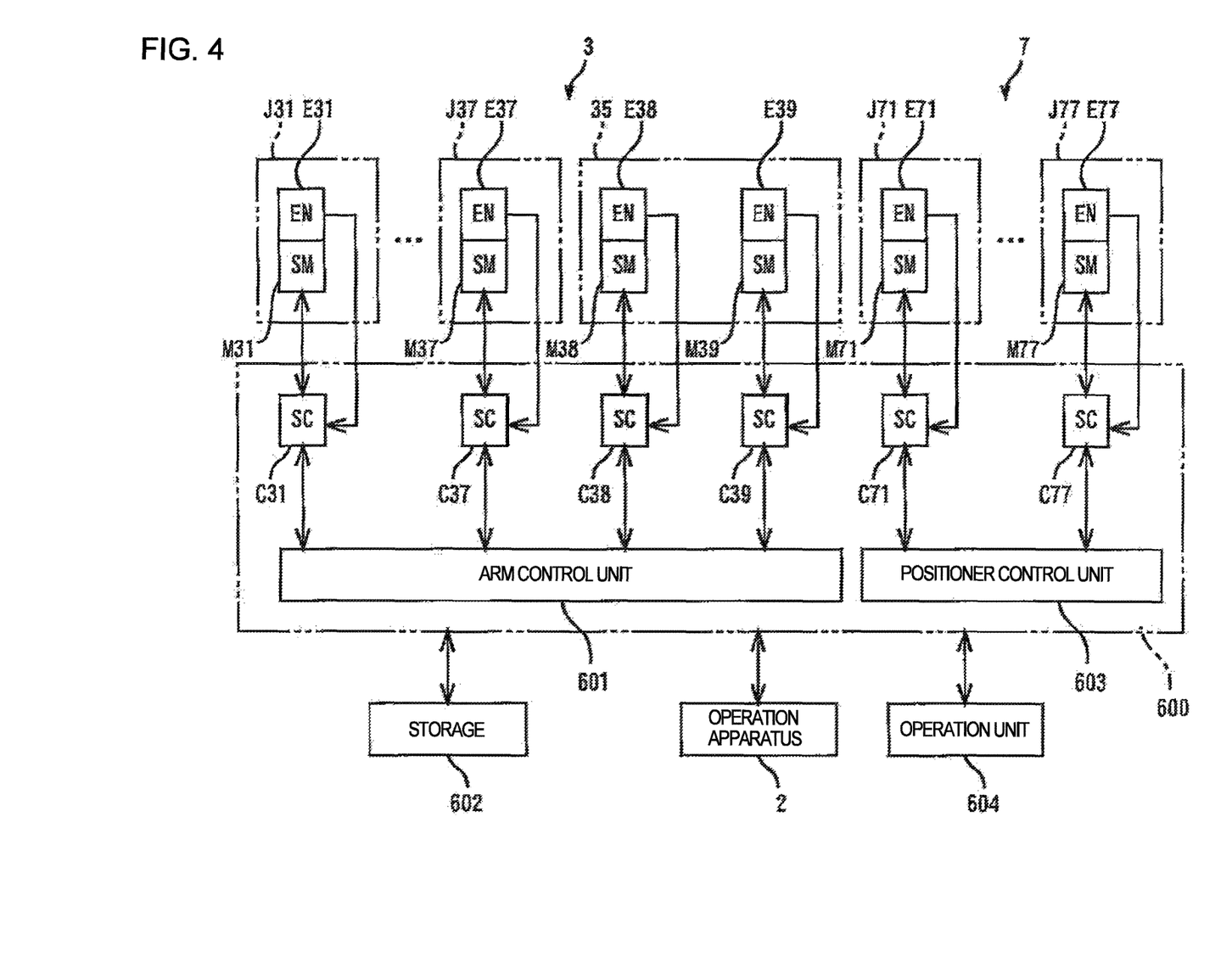
FIG. 4 is a block diagram illustrating a view of a schematic configuration of a control system of the manipulator arm of the surgical system illustrated in FIG. 1.

FIG. 4 is a block diagram illustrating a schematic configuration of a control system of the manipulator arm of the surgical system illustrated in FIG. 1. The arm body 30 having the above-described configuration is provided with driving servomotors (indicated as SM in FIG. 4) M31 to M37, encoders (indicated as EN in FIG. 4) E31 to E37 detecting rotation angles of the servomotors M31 to M37, and reduction drives (not illustrated) reducing the outputs of the servomotors M31 to M37 to increase the torque, with each corresponding to the joints J31 to J37 of the arm 3. Likewise, the positioner 7 is provided with driving servomotors M71 to M77, encoders E71 to E77 detecting rotation angles of the servomotors M71 to M77, and reduction drives (not illustrated) reducing the outputs of the servomotors M71 to M77 to increase the torque, with each corresponding to the joints J71 to J77 of the positioner 7.

Among the joints J31 to J37 and J71 to J77 in FIG. 4, the control systems of the first joint J31 and the seventh joint J37 of the arm 3 and the control systems of the first joint J71 and the seventh joint J77 of the positioner 7 are illustrated as a representative, and the control systems of the other joints J33 to J36 and J72 to J76 are omitted. In addition, the translation unit 35 is provided with a servomotor M38 for the translational movement, a servomotor M39 for the turn movement about the rotational axis 64, encoders E38 and E39 detecting rotation angles of the servomotors M38 and M39, and reduction drives (not illustrated) reducing the outputs of the servomotors M38 and M39 to increase the torque.

The encoders E31 to E39 and E71 to E77 are provided as an example of rotation position detection units for detecting the rotation positions (the rotation angles) of the servomotors M31 to M39 and M71 to M77. Rotation position detection units such as resolvers may be used instead of the encoders E31 to E39 and E71 to E77. The above-described elements of the drive systems of the arm 3 and wirings and control units for the elements are made of high-temperature resistant materials and have the heat resistance for sterile processing.

The controller 600 includes an arm control unit 601 that controls the movements of the arms 3 based on the action instructions and a positioner control unit 603 that controls the movement of the positioner 7. Servo-control units C31 to C39 are electrically connected to the arm control unit 601, and the servomotors M31 to M39 are electrically connected to the arm control unit 601 via not-illustrated amplifier circuits and the like. Likewise, servo-control units C71 to C77 are electrically connected to the positioner control unit 603, and the servomotors M71 to M79 are electrically connected to the positioner control unit 603 via not-illustrated amplifier circuits and the like.

In the above-described configuration, based on the action instruction inputted to the operation apparatus 2 during procedure, a position and orientation instruction of the distal end portion of the arm 3 is inputted to the arm control unit 601. Based on the position and orientation instruction and the rotation angles detected by the encoders E31 to E39, the arm control unit 601 generates position instruction values and outputs the thus-generated position instruction values. The servo-control units C31 to C39 receive the position instruction values, and then generate drive instruction values (torque instruction values) based on the rotation angles detected by the encoders E31 to E39 and the received position instruction values and output the thus-generated drive instruction values. The amplifier circuits receive the drive instruction values, and then supply drive currents corresponding to the received drive instruction values to the servomotors M31 to M39. As described above, the servomotors M31 to M39 are servo-controlled such that the distal end portion of the arm 3 is set at the position and orientation corresponding to the position and orientation instruction.

The controller 600 includes a storage 602 that can read out data to the arm control unit 601. The storage 602 stores in advance surgery information that is inputted through the operation apparatus 2. The surgery information includes information that indicates what types of the arms 3 are to be used together in surgery.

The storage 602 stores information such as the length of a surgical tool (the endoscope assembly or the instrument) held by the distal end portion of the arm 3 along the axis direction Dt. This allows the arm control unit 601 to grasp the position of the distal end portion of the surgical tool held by the distal end portion of the arm 3 based on the position and orientation instruction of the distal end portion of the arm 3.

In addition, the storage 602 stores in advance the preparation position for the positioner 7, the arm base 5, and the arms 3 (for example, positions and orientations of the elements 7, 5, and 3 illustrated in FIG. 1) that is determined before procedure. The storage 602 can store the preparation positions in accordance with a detail (type) of surgery, a surgery site, and so on. In addition, the storage 602 stores in advance a storing position. The storing position is set as the position and orientation in which the positioner 7 and the arms 3 are folded as much as possible so as to prevent the arms 3 and the like from coming into contact with a wall of the surgery room or other surgical equipment and the like while moving by the wagon 70.

Based on an instruction for operation (control input) such as setting of the preparation position inputted to the operation unit 604, the positioner control unit 603 controls the positioner 7, the arm base 5, and the arms 3 to move to the preparation position stored in the storage 602.

In procedure using the patient-side system 1 having the above-described configuration, first, the surgical assistant O (or the surgeon him/herself) moves the patient-side system 1 closer to the operating table 111 using the wagon 70. In this process, the positioner 7, the arm base 5, and the arms 3 are set at the storing position (not illustrated) set with respect to the wagon 70.

After the patient-side system 1 is moved, the surgical assistant O uses the operation unit 604 to selectively input the preparation position in accordance with the surgery type for the patient P. In this way, the positioner control unit 603 reads the information on the corresponding preparation position from the storage 602 and controls the operations of the positioner 7, the arm base 5, and the arms 3 such that these elements are set in the preparation position.

It is also possible to use the operation unit 604 to independently adjust the positions of the positioner 7, the arm base 5, and the arms 3 from the preparation position. Additionally, the surgical assistant O also can independently move the arms 3 from the preparation position by grasping the arms 3 and the like. With such preliminary operations, the positions of the positioner 7, the arm base 5, and the arms 3 are determined such that the sleeve (cannula sleeve) placed on the body surface of the patient P as the surgery site 110 and the surgical tools 40 attached to the arms 3 have an initial position relationship.

In an embodiment, the controller 600 does not receive the operation outputted from the operation apparatus 2 until the patient-side system 1 (the positioner 7, the arm base 5, and the arms 3) is set from the storing position to the preparation position. After the patient-side system 1 is set in the preparation position, the controller 600 can start to receive the operation outputted from the operation apparatus 2. During the procedure after the patient-side system 1 is set in the preparation position, the controller 600 properly changes the positions and orientations of the surgical tools 40 by controlling the operations of the arms 3 in response to the action instruction from the operation apparatus 2 while, in principle, keeping the positioner 7 and the arm base 5 still.

As described above, the preparation position illustrated in FIG. 1 is set as a position before procedure, in which the arm base 5 and the operating table 111 or the patient P have a predetermined position relationship. In this preparation position, the first rotation axis V1 (described later) in the positioner attachment portion 51 of the arm base 5 is inclined with respect to both a horizontal plane (a first plane S1) and a vertical plane (a second plane S2) including the longitudinal direction (a first direction D1) of the arm base 5 and perpendicular to the horizontal plane, with the arm base 5 positioned such that the longitudinal direction of the arm base 5 is parallel to the horizontal plane (the first plane S1). In other words, the first rotation axis V1 is inclined with respect to the vertical direction and inclined with respect to the horizontal direction. In order to easily achieve the above-described preparation position, the arm base 5 of this embodiment have the following configuration.

Figure 5A:
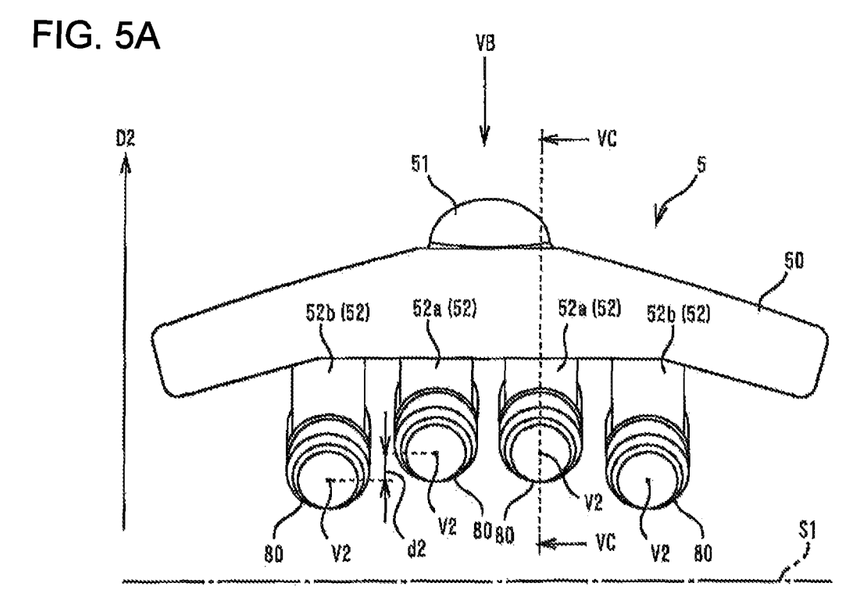
FIG. 5A is a diagram illustrating a schematic view of a configuration of the arm base in the surgical system illustrated in FIG. 1.
Figure 5B:
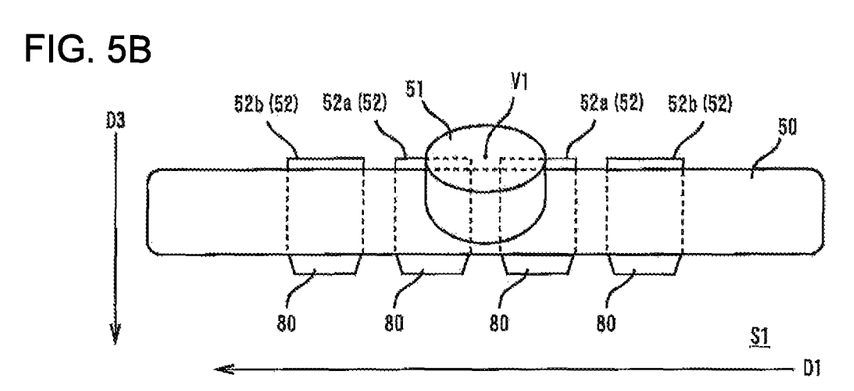
FIG. 5B is a diagram illustrating a schematic view of the configuration of the arm base in the surgical system illustrated in FIG. 1.
Figure 5C:
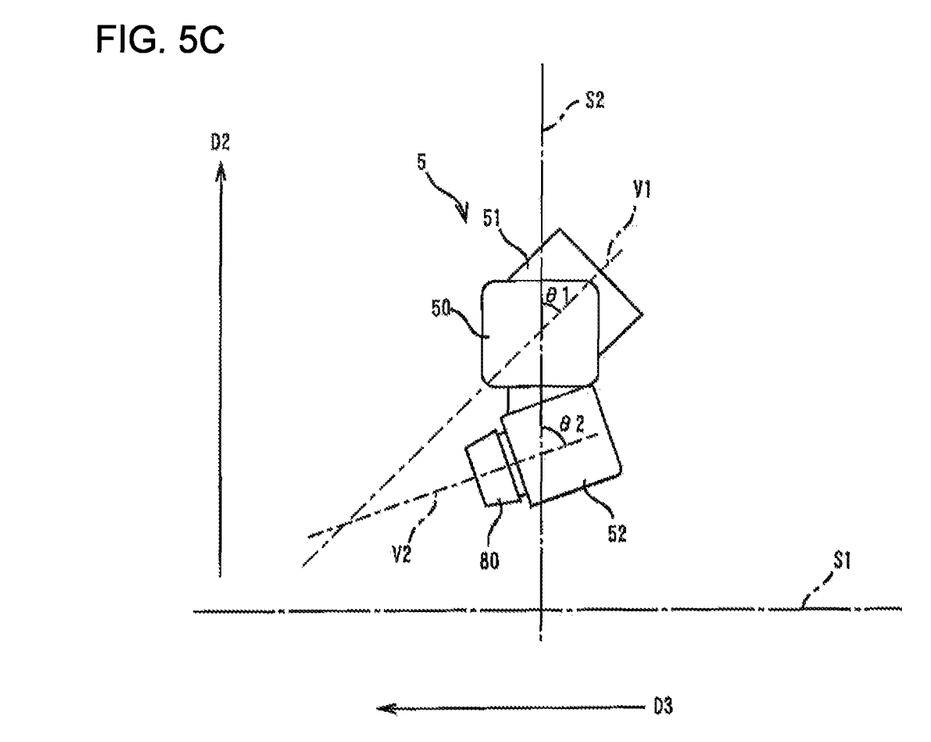
FIG. 5C is a diagram illustrating a schematic view of the configuration of the arm base in the surgical system illustrated in FIG. 1.

FIGS. 5A to 5C are schematic views illustrating a configuration of the arm base in the surgical system illustrated in FIG. 1. FIG. 5A is a front view as seen from the front side (from the VA direction in FIG. 1) in the preparation position illustrated in FIG. 1, FIG. 5B is a top view as seen from the VB direction illustrated in FIG. 5A, and FIG. 5C is a cross-sectional view taken along the VC-VC indicated in FIG. 5A.

The arm attachment portions 52 are formed as follows. As illustrated in FIG. 5B, in a plan view of the first plane 51, the base end portions of the arms 3 (the bases 80) are aligned in the predetermined first direction D1 that is included in the first plane 51. The first plane 51 is a virtual plane parallel to a floor surface (a horizontal plane) G with the arm base 5 set in the preparation position (FIG. 1). That is, the arm attachment portions 52 are aligned in the first direction D1 (a direction going away from the paper surface of FIG. 1) when the arm base 5 set in the preparation position is seen from above.

In addition, the position of the base end portion of at least one of the arms 3 in the second direction (the vertical direction) D2 perpendicular to the first plane 51 is configured to be different from the base end portions of the other arms 3 in the second direction D2. In FIGS. 5A and 5B, among the aligned four arm attachment portions 52, two arm attachment portions on the inner side are inner arm attachment portions 52a while the other two arm attachment portions on the outer side are outer arm attachment portions 52b. The position of the base 80 of the arm 3 attached to each of the inner arm attachment portions 52a (in FIG. 5A, the position is based on the second rotation axis V2 as the rotation axis of the first joint J31) is higher by a predetermined distance d2 than the position of the base 80 of the arm 3 attached to each of the outer arm attachment portions 52b.

In each of the arm attachment portions 52 (52a or 52b), the base end portion of is attached on a lower surface of the arm base body 50, the distal end portion extends downward (in the second direction D2), and the distal end portion is provided with a fitting portion to which the base 80 of the arm 3 is detachably attached. The length of an extending portion of the inner arm attachment portion 52a in the second direction D2 is shorter than the length of an extending portion of the outer arm attachment portion 52b in the second direction D2. Consequently, while the arms 3 are attached to the arm attachment portions 52, the positions in the second direction D2 of the outer two of the arms 3 are set lower than the positions in the second direction D2 of the inner two of the arms 3 (closer to the patient P in the preparation position).

As illustrated in FIG. 5C, the positioner attachment portion 51 extends from the top of the arm base body 50 in the first rotation axis V1 direction. The first rotation axis V1 is configured to be inclined with respect to the virtual second plane S2 including the first and second directions D1 and D2.

In addition, the arm attachment portions 52 are non-rotatably secured to the arm base body 50 such that the attachment directions of the arms 3 are set in the same direction. More specifically, as illustrated in FIGS. 5B and 5C, the positioner attachment portion 51 is formed to extend from the top of the arm base body 50 toward one side in a third direction D3 that is perpendicular to the second plane S2, and the arm attachment portions 52 are formed to extend from the bottom of the arm base body 50 toward the other side in the third direction D3.

Moreover, as illustrated in FIG. 5C, the arm attachment portions 52 are configured to hold the arms 3 such that the second rotation axis V2 of each arm 3 is inclined with respect to the second plane S2. In this case, an angle of inclination θ1 of the first rotation axis V1 with respect to the second plane S2 is smaller than an angle of inclination θ2 of the second rotation axis V2 with respect to the second plane S2. In other words, the angle formed by the arm attachment direction of the arm attachment portion 52 is more horizontal than the angle formed by the direction of the first rotation axis V1. Thus, an extension of the first rotation axis V1 and an extension of the second rotation axis V2 cross each other. For example, the angle of inclination θ1 of the first rotation axis V1 with respect to the second plane S2 is around 45° (an angle of inclination of the first rotation axis V1 with respect to the first plane S1 is also around) 45°, while the angle of inclination θ2 of the second rotation axis V2 with respect to the second plane S2 is around 60° (an angle of inclination of the second rotation axis V2 with respect to the first plane S1 is around 30°).

According to the above-described configuration, the rotation axis (the first rotation axis V1) of the positioner attachment portion 51 is directed to the vicinity of the surgery site 110 when the arm base 5 is positioned obliquely above the surgery site (the position of the sleeve) 110 so as to oppose the patient P with the arm attachment portions 52 positioned below the arm base body 50. With this, when the positioner 7, the arm base 5, and the arms 3 are set in the preparation position stored in the storage 602 as illustrated in FIG. 1, the longitudinal direction of the arm base 5 in which the arms 3 are aligned is parallel to the horizontal plane, and the first rotation axis V1 that allows the distal end portion of the positioner 7 to relatively rotate with respect to the arm base 5 in the positioner attachment portion 51 of the arm base 5 is inclined with respect to both the horizontal plane and the vertical plane including the longitudinal direction of the arm base 5 and perpendicular to the horizontal plane. This makes it possible to arrange the arm base 5 in a position in which the extension of the first rotation axis V1 passes through the vicinity of the surgery site 110.

Consequently, it is possible to set the positions of the arm base 5 and the positioner 7 in the horizontal direction in positions offset from the surgery site 110 with respect to the position of the surgery site 110 in the horizontal direction. This can make the patient P or the operator who prepares the surgery less oppressed. In addition, this makes it easy to arrange the arms 3 to direct obliquely downward (toward the vicinity of the surgery site) from the arm base 5. Moreover, when the arm base 5 is turned about the first rotation axis V1 with respect to the distal end portion of the positioner 7 (the sixth link 96) because, for example, the surgery site 110 is inclined with respect to a direction perpendicular to the floor surface G, the arms 3 can be opposed to the surgery site 110 without changing the orientations of the arms 3 with respect to the surgery site 110. Thus, according to the above-described configuration, it is possible to increase the three-dimensional movement range of the arms 3 based on the surgery site 110 of the patient P and to avoid the interference between the arms 3 to make it easy to arrange the arms 3 in proper positions.

According to one or more embodiments described above, the rotational axis of the sixth joint J7 serving as a second roll joint of this disclosure is inclined with respect to the rotational axis of the seventh joint J77 serving as a first roll joint of this disclosure. With this configuration, the entire of the arm base 5 can be turned in the circumferential direction around the patient P while keeping the sixth link 96 of the positioner 7 directed to the patient. Thus, the arm base 5 can be easily set in a position where the arms 3 are easily moved in the three-dimensional directions with reference to the surgery site 110 of the patient.

According to one or more embodiments described above, the fifth link 95 and the fourth link 94 are connected by means of the fifth joint J75 serving as a first pivotal joint of this disclosure. With this configuration, the positioner 7 can moves the arm base 5 upwardly and downwardly. This makes it easy to perform positional adjustments of the arms 3 with respect to the surgery site 110 of the patient.

According to one or more embodiments described above, the first link 91 and the wagon 70 is connected by means of the first joint J71 serving as a third roll joint of this disclosure. With this configuration, the positioner 7 can be rotated with respect to the wagon 70 about the vertical axis. This improves the degrees of freedom upon positioning the wagon 70 with respect to the patient.

According to one or more embodiments described above, the patient-side system 1 includes the operation unit 604 that controls the positioner 7 to move the arm base 5. With this configuration, the operator who performs preparations of the surgery can easily position the arm base 5.

According to one or more embodiments described above, the arm attachment portions 52 are formed to extend from the bottom of the arm base body 50 to the other side in the third direction D3. This makes it easy to arrange the arms 3 to direct obliquely downward (toward the vicinity of the surgery site) from the arm base 5.

According to one or more embodiments described above, in the preparation position, the connection portion between the first portion 81a and the second portion 81b in the first link 81 of the arm 3 (the bending portion of the first link 81) directs downward. That is, the orientation of the first link 81 in the preparation position is a downward protrusion. Since this brings slightly up the arm 3 extending obliquely downward from the arm base 5, the arm 3 in the preparation position can extend in a more horizontal direction (in the horizontal direction, the surgery site 110 and the positions of the positioner 7 and the arm base 5 are more away from each other).

According to one or more embodiments described above, in the preparation position, the fourth link 84 of the arm 3 is an arm link portion positioned at the highest among the arm link portions. In this case, the connection portion between the first portion 84a and the second portion 84b in the fourth link 84 (the bending portion of the fourth link 84) directs upward. That is, the orientation of the fourth link 84 in the preparation position is an upward protrusion. Accordingly, in the preparation position, the entire orientation of the arm 3 is a folded orientation as the upward protrusion. This makes it possible to secure a wide space (work space) above (directly above) the surgery site 110 with the arms 3 extending obliquely downward from the arm base 5. In addition, as described above, since the link length of the arm link portion (the fourth link 84) at the peak of the arm 3 in the preparation position is short, the folded orientation of the arm 3 in the preparation position can be compact.

According to one or more embodiments described above, in the preparation position, the translation unit 35 is positioned such that the axis direction Dt is orthogonal to the longitudinal direction of the sixth link 86 of the arm 3. Thus, in the preparation position, the distal end portion of the arm 3 (the sixth link 86) extends in a direction obliquely downward from the fourth link 84 positioned at the peak of the arm 3 to be away from the arm base 5, while the surgical tool 40 extends in a direction obliquely downward toward the arm base 5.

According to one or more embodiments described above, at least one of the arm link portions forming the arm 3 is bent, Thus, it is possible to make the surgical tool 40 attached to the distal end portion of the arm 3 extending obliquely downward from the arm base 5 easy to extend in a direction orthogonal to the attachment direction of the arm 3 in the arm base 5.

Consequently, it is possible to effortlessly direct the surgical tool 40 to the surgery site 110 by positioning the arm 3 such that the vicinity of the peak of the arm 3 is positioned above (directly above) the surgery site 110. This makes it possible to arrange the arms 3 in proper positions for performing procedure before starting the procedure.

According to one or more embodiments, the translation unit 35 is configured to be rotatable in both directions about the rotation axis of the seventh joint J37 with respect to the sixth link 86 of the arm 3 also in the preparation position. More specifically, the translation unit 35 is formed such that the preparation position is the middle position during the rotation about the rotation axis of the seventh joint J37 with respect to the sixth link 86. This makes it possible to increase a range of the position adjustment from the state in which the axis direction Dt of the surgical tool 40 is directing the surgery site 110 of the patient P.

According to one or more embodiments as described above, in one of the positioner link portions (the sixth link 96) attached to the positioner attachment portion 51 of the arm base 5, both the sixth joint J76 on the base end side and the seventh joint J77 on the distal end side are formed as roll joints, and the rotation axis of the sixth joint J76 is relatively inclined with respect to the rotation axis of the seventh joint J77. This makes it possible to turn the entirety of the arm base 5 in the circumferential direction of the patient P while directing the arm attachment portion 52 of the arm base 5 to the patient P. Consequently, the position of the arm base 5 can be easily adjusted to a position in which the arms 3 are three-dimensionally moved easily based on the surgery site 110 of the patient P.

According to the above descriptions, many improvements and modifications of the above one or more embodiments are apparent to the person skilled in the art. Thus, the above descriptions should be construed as only an example, and the above descriptions are provided for teaching one or more aspects for executing the invention to the person skilled in the art. It is possible to practically change the details of the configuration and/or function of the above described one or more embodiments without departing from the spirit of the invention.

For example, in the above-described one or embodiments, there is described an example of a configuration in which the difference between the heights of the base end portions (the positions in the second direction D2) of the arms 3 attached to the arm attachment portions 52 (52a, 52b) of the arm base 5 are made based on the difference between the lengths of the extending portions of the arm attachment portions 52 (52a, 52b) in the second direction D2; however, it is not limited thereto. For example, the difference between the heights of the base end portions of the arms 3 may be made based on the difference between the attachment positions of the arm attachment portions 52 to the arm base body 50 in the second direction D2. For example, at least two end portions of the lower surface of the arm base body 50 may have inclined surfaces that are inclined with respect to the horizontal plane (surfaces inclined downward as being closer to the end portions), and at least two outer arm attachment portions 52b may be attached to the inclined surfaces.

In the above-described one or more embodiments, there is described an example of a configuration in which the lower surface of the arm base body 50 (the surface to which the arm attachment portions 52 are attached) is formed as a flat surface; however, it is not limited thereto. The lower surface of the arm base body 50 may be a curved surface (for example, a cross section perpendicular to the third direction D3 is an arc shape having the center on the patient P side). In the above-described one or more embodiments, the lower surface of the arm base body 50 is provided with inclined surfaces on the two end portions in the first direction D1; however, it is not limited thereto. The lower surface of the arm base body 50 may have no inclined surfaces. Otherwise, the lower surface of the arm base body 50 may be formed such that the central portion of the lower surface in the first direction D1 is the peak and two surfaces are inclined downward from the peak toward the end portions in the first direction D1 (to be closer to the patient P).

In the above-described one or more embodiments, there is described an example of an aspect in which the positioner attachment portion 51 is provided to be inclined with respect to the arm base body 50, and the first rotation axis V1 is inclined with respect to both the horizontal plane (the floor surface G) and the vertical plane perpendicular to the horizontal plane in the preparation position; however, it is not limited thereto. For example, the first rotation axis V1 may be in the same direction as the direction in which the arm attachment portions 52 are attached to the arm base body 50. That is, in this case, the entirety of the arm base 5 may be inclined with respect to both the horizontal plane and the vertical plane perpendicular to the horizontal plane.

In the arm attachment portions 52, the position of the base end portion of one of the arms 3 in the height direction (the second direction D2) may be different from the positions of the base end portions of the rest of the arms 3 in the height direction. In the above-described one or more embodiments, there is described a configuration in which the four arm attachment portions 52 are provided to the corresponding four arms 3; however, it is not limited thereto. The multiple (two, three, or four) arms 3 may be attached to a single arm attachment portion 52.

The number (the number of the degrees of freedom) and shapes of the joints (the link portions) in the arms 3 and/or the positioner 7 are not limited to the above-described one or more embodiments, and various aspects can be employed therefor.

As described above, one or more embodiments of this disclosure may be useful for making the operator who performs preparations of the surgery less oppressed and avoid interference between manipulator arms to make it easy to arrange the arms in proper positions.

Note that aspects of the above-described one or more embodiments may also be specified in the following paragraphs.

An arm base according to an aspect includes: an arm base body; a positioner attachment portion that is attached to the arm base body, with a distal end portion of a positioner extending from a predetermined base attached to the positioner attachment portion while being relatively rotatable about a predetermined first rotation axis; and at least one arm attachment portion that is attached to the arm base body, with a base end portion of each of manipulator arms attached to the arm attachment portions, the manipulator arms having the multi-degree of freedom. The arm attachment portions are formed as follows. In a predetermined plan view of a first plane, the base end portions of the manipulator arms are aligned in a predetermined first direction that is included in the first plane. Also, the position of the base end portion of at least one of the manipulator arms in a second direction perpendicular to the first plane is different from the positions of the base end portions of the rest of the manipulator arms in the second direction. The first rotation axis is configured to be inclined with respect to the second plane including the first and second directions.

According to the arm base of this aspect, a rotation axis of the positioner attachment portion is directed to the vicinity of a surgery site when the arm base is positioned obliquely above the surgery site so as to oppose the patient with the arm attachment portions positioned below the arm base body. Consequently, it is possible to set the positions of the arm base and the positioner in the horizontal direction in positions offset from the surgery site with respect to the position of the surgery site in the horizontal direction. This can make a patient or an operator less oppressed. In addition, this makes it easy to arrange the manipulator arms to direct obliquely downward (toward the vicinity of the surgery site) from the arm base. Thus, it is possible to increase the three-dimensional movement range of the manipulator arms based on the surgery site of the patient and to avoid the interference between the manipulator arms to make it easy to arrange the arms in proper positions.

In the arm base of this aspect, the base end portion of each of the manipulator arms may be attached to the corresponding arm attachment portion with being relatively rotatable about a predetermined second rotation axis that is configured to be inclined with respect to the second plane, wherein the positioner attachment portion is formed to extend from the top of the arm base body toward one side in a third direction that is perpendicular to the second plane, and the arm attachment portions are formed to extend from the bottom of the arm base body toward the other side in the third direction. With this configuration, it may be easier to arrange the manipulator arms to direct obliquely downward (toward the vicinity of the surgery site) from the arm base.

A surgical system according to an aspect may include: manipulator arms with multi-degree of freedom that each include a distal end portion provided with a tool holding unit capable of holding an elongated surgical tool; an arm base to which base end portions of the manipulator arms are connected; a positioner that connects a predetermined base and the arm base; a controller that controls actions of the positioner, the arm base, and the manipulator arms; and a storage that stores a predetermined preparation position for the positioner, the arm base, and the manipulator arms that is determined before procedure. Based on a predetermined control input, the controller controls the positioner, the arm base, and the manipulator arms to be moved to the preparation position stored in the storage. The arm base includes: an arm base body; a positioner attachment portion to which a distal end portion of the positioner is attached while being relatively rotatable about a predetermined first rotation axis; and at least one arm attachment portion to which a base end portion of each of the manipulator arms is attached. The manipulator arms are aligned along a longitudinal direction of the arm base. In the preparation position, the first rotation axis is inclined with respect to both a horizontal plane and a vertical plane including the longitudinal direction of the arm base and perpendicular to the horizontal plane, with the arm base positioned such that the longitudinal direction of the arm base is parallel to the horizontal plane.

According to the surgical system of this aspect, when the positioner, the arm base, and the manipulator arms are set in the preparation position stored in the storage, the longitudinal direction of the arm base in which the manipulator arms are aligned is parallel to the horizontal plane, and the first rotation axis that allows the distal end portion of the positioner to relatively rotate with respect to the arm base in the positioner attachment portion of the arm base is inclined with respect to both the horizontal plane and the vertical plane including the longitudinal direction of the arm base and perpendicular to the horizontal plane. This makes it possible to arrange the arm base in a position in which the extension of the first rotation axis passes through the vicinity of the surgery site. Consequently, it is possible to set the positions of the arm base and the positioner in the horizontal direction in positions offset from the surgery site with respect to the position of the surgery site in the horizontal direction. This can make a patient or an operator less oppressed. In addition, this makes it easy to arrange the manipulator arms to direct obliquely downward (toward the vicinity of the surgery site) from the arm base. Thus, it is possible to increase the three-dimensional movement range of the manipulator arms based on the surgery site of the patient and to avoid the interference between the manipulator arms to make it easy to arrange the arms in proper positions.

In the surgical system of this aspect, each manipulator arm may include multiple arm link portions connected with multiple joint portions such that one arm link portion is rotatably connected to another arm link portion sequentially, wherein at least one of the arm link portions include a first portion extending from the joint portion on the base end side in a predetermined direction, and a second portion extending from a distal end portion of the first portion in a direction crossing with the extending direction of the first direction to be connected to the joint portion on the distal end side. With this configuration, since at least one of the arm links can be bent, it may be possible to secure a wide space above the surgery site with the manipulator arms extending obliquely downward from the arm base.

In the surgical system of this aspect, the positioner may include multiple positioner link portions connected with multiple joint portions such that one positioner link portion is rotatably connected to another positioner link portion sequentially, wherein, in one of the positioner link portions that is attached to the positioner attachment portion of the arm base, both the joint portion on the base end side and the joint portion on the distal end side are formed as roll joints, wherein the rotation axis of the joint portion on the base end side is relatively inclined with respect to the rotation axis of the joint portion on the distal end side. With this configuration, it may be possible to turn the entirety of the arm base in the circumferential direction of the patient while directing the arm attachment portion of the arm base to the patient. Consequently, the position of the arm base can be easily adjusted to a position in which the manipulator arms are three-dimensionally moved easily based on the surgery site of the patient.

The invention claimed is:

1. A patient-side apparatus of a surgical system, comprising:
   three or more manipulator arms with multi-degree of freedom, each of which includes a distal end portion provided with a tool holding part configured to hold an elongated surgical tool;
   an arm base on which base end portions of the three or more manipulator arms are directly attached at different positions of the arm base;
   a base; and
   a positioner that includes links and joints to connect the base and the arm base such that the positioner movably holds the arm base, wherein
   the links include a first link that is connected to a central portion of the arm base in a longitudinal direction of the arm base with a first roll joint arranged between the first link and the arm base, and
   the positioner holds the arm base such that a first rotation axis of the first roll joint is inclined with respect to both a vertical direction and a horizontal plane, wherein
   the links include a second link connected to the first link with a second roll joint arranged therebetween, and
   the links include a third link connected to the second link with a pivotal joint arranged therebetween such that the second link is rotatable about a pitch axis of the pivotal joint with respect to the third link.

2. The patient-side apparatus according to claim 1, wherein
   the positioner is an articulated robot with six or more degrees of freedom.

3. A patient-side apparatus of a surgical system, comprising:
   three or more manipulator arms with multi-degree of freedom, each of which includes a distal end portion provided with a tool holding part configured to hold an elongated surgical tool;
   an arm base on which base end portions of the three or more manipulator arms are directly attached at different positions of the arm base;
   a base; and
   a positioner that includes links and joints to connect the base and the arm base such that the positioner movably holds the arm base, wherein
   the links include a first link that is connected to a central portion of the arm base in a longitudinal direction of the arm base with a first roll joint arranged between the first link and the arm base,
   the positioner holds the arm base such that a first rotation axis of the first roll joint is inclined with respect to both a vertical direction and a horizontal plane,
   the links include a second link connected to the first link with a second roll joint arranged therebetween, a second rotation axis of the second roll joint is inclined with respect to the first rotation axis of the first roll joint, and
   the links include a third link connected to the second link with a pivotal joint arranged therebetween such that the second link is rotatable about a pitch axis of the pivotal joint with respect to the third link.

4. The patient-side apparatus according to claim 1, wherein
   the arm base comprises:
   an arm base body;
   a positioner attachment portion that is attached to the arm base body, with the first link attached to the positioner attachment portion with the first roll joint arranged therebetween; and
   arm attachment portions that are attached to the arm base body, with the base end portions of the three or more manipulator arms directly attached to the arm attachment portions.

5. The patient-side apparatus according to claim 4, wherein
   the arm attachment portions are aligned along the longitudinal direction of the arm base.

6. The patient-side apparatus according to claim 4, wherein
   the base end portion of each of the three or more manipulator arms is directly attached to a corresponding arm attachment portion of the arm base such that the base end portion is rotatable about a roll axis with respect to the corresponding arm attachment portion.

7. The patient-side apparatus according to claim 1, further comprising:
   an operation unit that issues an instruction to cause the positioner to move the arm base.

8. The patient-side apparatus according to claim 7, further comprising:
   a controller that controls movements of the positioner and the three or more manipulator arms; and
   a storage that stores a preparation position for the positioner, the arm base, and the three or more manipulator arms before surgery, wherein
   based on the instruction from the operation unit, the controller controls the positioner, the arm base, and the three or more manipulator arms to be moved to the preparation position stored in the storage, and
   in the preparation position, the positioner holds the arm base with the first rotation axis of the first roll joint inclined with respect to both the vertical direction and the horizontal plane.

9. A surgical system, comprising:
   a patient-side apparatus including three or more manipulator arms with multi-degree of freedom, each of which includes a distal end portion provided with a tool holding part configured to hold an elongated surgical tool; and
   an operation apparatus to remotely control the three or more manipulator arms in surgery, wherein
   the patient-side apparatus comprises:
   an arm base on which base end portions of the three or more manipulator arms are directly attached at different positions of the arm base;
   a base; and
   a positioner that includes links and joints to connect the base and the arm base such that the positioner movably holds the arm base, wherein
   the links include a first link that is connected to a central portion of the arm base in a longitudinal direction of the arm base with a first roll joint arranged between the first link and the arm base,
   the positioner holds the arm base such that a first rotation axis of the first roll joint is inclined with respect to both a vertical direction and a horizontal plane,
   the links include a second link connected to the base with a second roll joint arranged therebetween, and
   the links include a third link connected to the second link with a pivotal joint arranged therebetween, such that the second link is rotatable about a pitch axis of the pivotal joint with respect to the third link.

10. The surgical system according to claim 9, wherein
    the positioner is an articulated robot with six or more degrees of freedom.

11. The surgical system according to claim 9, wherein the links include the second link connected to the first link with the second roll joint arranged therebetween, wherein a second rotation axis of the second roll joint is inclined with respect to the first rotation axis of the first roll joint.

12. A surgical system, comprising:

a patient-side apparatus including three or more manipulator arms with multi-degree of freedom, each of which includes a distal end portion provided with a tool holding part configured to hold an elongated surgical tool; and an operation apparatus to remotely control the three or more manipulator arms in surgery, wherein the patient-side apparatus comprises:
- an arm base on which base end portions of the three or more manipulator arms are directly attached at different positions of the arm base;
- a base; and
- a positioner that includes links and joints to connect the base and the arm base such that the positioner movably holds the arm base, the links include a first link that is connected to a central portion of the arm base in a longitudinal direction of the arm base with a first roll joint arranged between the first link and the arm base, the positioner holds the arm base such that a first rotation axis of the first roll joint is inclined with respect to both a vertical direction and a horizontal plane, the links include a second link connected to the first link with a second roll joint arranged therebetween, wherein a second rotation axis of the second roll joint is inclined with respect to the first rotation axis of the first roll joint, and the links include a third link connected to the second link with a pivotal joint arranged therebetween, such that the second link is rotatable about a pitch axis of the pivotal joint with respect to the third link.

13. The surgical system according to claim 9, wherein the arm base comprises:

an arm base body;

a positioner attachment portion that is attached to the arm base body, with the first link attached to the positioner attachment portion with the first roll joint arranged therebetween; and arm attachment portions that are attached to the arm base body, with the base end portions of the three or more manipulator arms directly attached to the arm attachment portions.

14. The surgical system according to claim 13, wherein the arm attachment portions are aligned along the longitudinal direction of the arm base.

15. The surgical system according to claim 13, wherein the base end portions of the three or more manipulator arms are directly attached to a corresponding arm attachment portion of the arm base such that each base end portion is rotatable about an axis of the base end portion.

16. The surgical system according to claim 9, wherein the patient-side apparatus further comprises an operation unit that issues an instruction to cause the positioner to move the arm base.

17. The surgical system according to claim 16, wherein the patient-side apparatus comprises:

a controller that controls movements of the positioner and the three or more manipulator arms; and a storage that stores a preparation position for the positioner, the arm base, and the three or more manipulator arms before surgery, wherein based on the instruction from the operation unit, the controller controls the positioner, the arm base, and the three or more manipulator arms to be moved to the preparation position stored in the storage, and in the preparation position, the positioner holds the arm base with the first rotation axis of the first roll joint inclined with respect to both the vertical direction and the horizontal plane.

* * * * *